Figure 1:
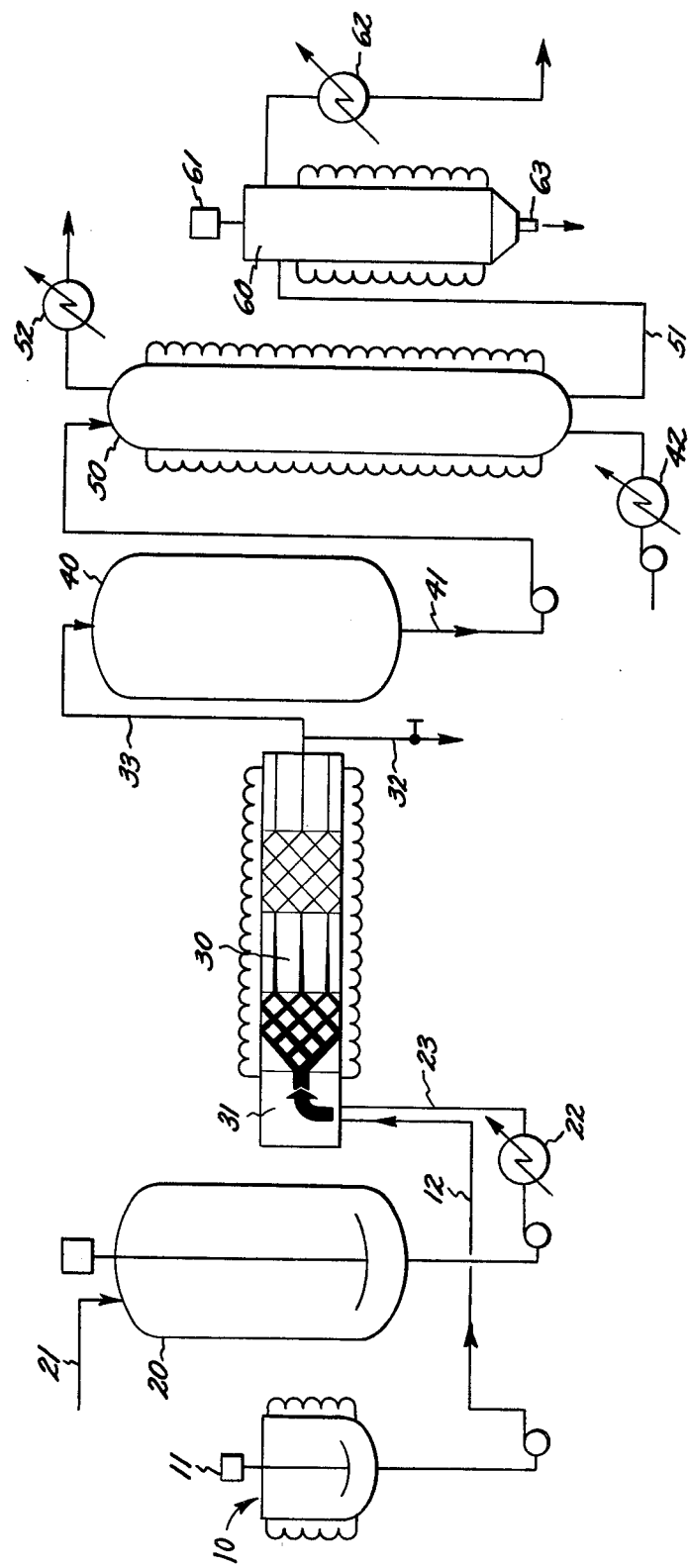

| United States Patent [19]
Webb et al.

[11] 4,329,291
[45] May 11, 1982

[54] METHOD FOR MAKING AROMATIC BIS(ETHER ANHYDRIDE)S

[75] Inventors: Jimmy L. Webb, Ballston Lake, N.Y.; Bharat M. Mehta, Pittsfield, Mass.

[73] Assignee: General Electric Company, Schenectady, N.Y.

[21] Appl. No.: 250,804

[22] Filed: Apr. 3, 1981

[51] Int. Cl.$^3$ .......................................... C07D 307/89
[52] U.S. Cl. .................................... 549/241; 562/468
[58] Field of Search ...................................... 260/346.3

[56] References Cited

U.S. PATENT DOCUMENTS 4,116,980  9/1978  Webb .............................. 260/346.3
4,128,574  12/1978  Markezich et al. ................. 562/473

Primary Examiner—Henry R. Jiles
Assistant Examiner—Bernard Dentz
Attorney, Agent, or Firm—William A. Teoli; James C. Davis, Jr.

[57] ABSTRACT

A method is provided for making aromatic bis(ether phthalic anhydride), for example, 2,2-bis[4-(3,4-dicarboxyphenoxy)phenyl]propane dianhydride by effecting an exchange reaction between molten aromatic bis(ether-imide) and phthalic anhydride in the presence of water and an imide-anhydride exchange catalyst. An enchanced rate of aromatic bis(ether phthalic anhydride) production has been found to occur, if the molten aromatic bis(ether imide) is contacted with the phthalic anhydride in the form of an aqueous feed mixture of phthalic acid and exchange catalyst and the resulting equilibrated mixture extracted with organic solvent.

5 Claims, 1 Drawing Figure

METHOD FOR MAKING AROMATIC BIS(ETHER ANHYDRIDE)S

CROSS REFERENCE TO RELATED APPLICATIONS

Reference is made to copending application Ser. No. 251,019, filed Apr. 3, 1981 of Jimmy L. Webb and Donald L. Phipps, Jr., for Method for Making Aromatic Bis(Ether Anhydride)s and our copending application Ser. No. 253,446, filed Apr. 13, 1981, for Method for Making Aromatic Bis(Ether Anhydride)s, and assigned to the same assignee as the present invention.

BACKGROUND OF THE INVENTION

Prior to the present invention, as shown by Webb, U.S. Pat. No. 4,116,980 and Markezich et al, U.S. Pat. No. 4,128,574, assigned to the same assignee as the present invention, aromatic bis(ether anhydride)s of the formula,

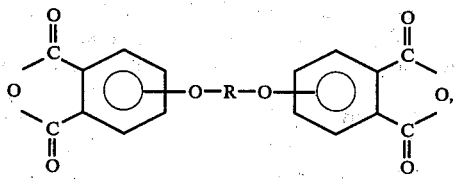

where R is a $C_{(6-30)}$ divalent aromatic organic radical, and the corresponding aromatic bis(ether dicarboxylic acid)s were made by effecting reaction between the appropriate aromatic bis(ether-imide) and aromatic anhydride in the presence of water and an imide-anhydride exchange catalyst. Imide-anhydride exchange was achieved by heating the imide-anhydride exchange reaction mixture at elevated temperatures in the presence of water.

An improvement was effected by Webb when the aforementioned mixture of aromatic bis(ether imide) and phthalic anhydride was heated under pressure in the presence of water and an N-organo aromatic imide was selectively removed from the liquid phase mixture by venting the vapor phase therefrom. Although the aforementioned procedure of heating the imide-anhydride exchange mixture under sealed conditions provides valuable exchange results, the procedure requires several hours of heating and venting before desirable yields of aromatic bis(ether anhydride) reaction product can be recovered from the exchange reaction mixture.

Efforts to improve the rate at which equilibrium was achieved in an imide-anhydride exchange reaction utilizing the aromatic bis(ether-imide) in molten form and contacting it with phthalic acid and water, often resulted in poor mixing of the aqueous feed stream with the molten aromatic bis(ether imide).

The present invention is based on the discovery that an aqueous phthalic acid exchange-catalyst solution having a phthalic anhydride concentration (25-35% by weight) or sufficient to provide a feed viscosity of at least 25 to 90 centipoises at 25° C., has been found to provide optimum mixing characteristics with molten aromatic bis(ether imide), of the formula,

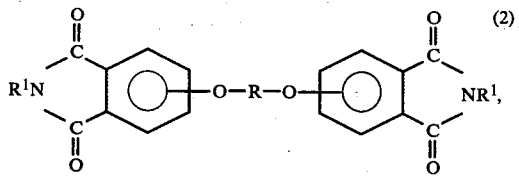

and significant improvements in the rate of production of aromatic bis(ether anhydride) of formula (1), where $R^1$ is a monovalent organo radical selected from the class consisting of $C_{(1-8)}$ alkyl radicals, and $C_{(6-13)}$ aromatic radicals.

STATEMENT OF THE INVENTION

In the process of making aromatic bis(ether anhydride) through an imide-anhydride exchange reaction comprising heating a mixture of aromatic bis(ether imide), phthalic anhydride, water and imide-anhydride exchange catalyst, whereby extended reaction periods, or venting of the reaction mixture is required to achieve an imide-anhydride exchange mixture at equilibrium having aromatic bis(anhydride), the improvement which comprises, forming the imide-anhydride reaction mixture by intermixing the aromatic bis(ether imide) while in the molten state and in the presence of an aqueous mixture of phthalic acid and thereafter extracting the imide-anhydride exchange mixture with an organic solvent.

Radicals included by R are more particularly

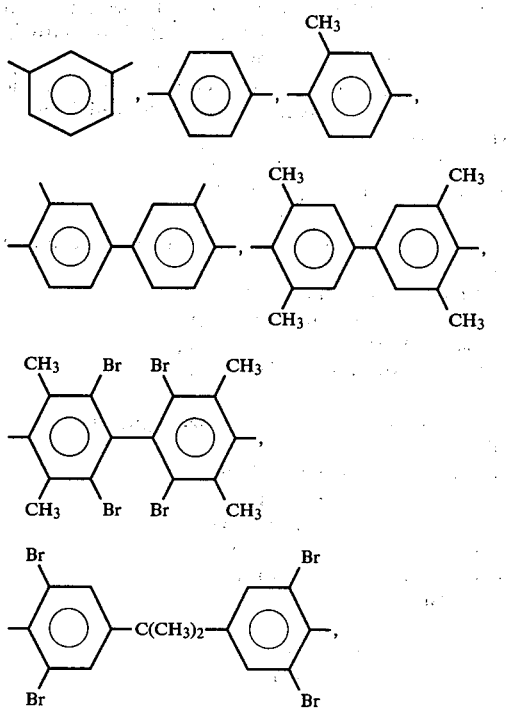

and divalent organic radicals of the general formula,

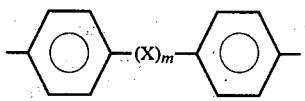

where X is a member selected from the class consisting of divalent radicals of the formulas,

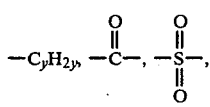

—O—, and —S—, where m is 0 or 1, and y is a whole number from 1 to 5.

Radicals included by $R^1$ are, for example, phenyl, tolyl, xylyl, naphthyl, chlorophenyl, bromonaphthyl, etc., and alkyl radicals, such as methyl, ethyl, etc.

As further shown in U.S. Pat. No. 3,879,428, the aromatic bis(ether phthalimide)s of formula (2) can be made by effecting reaction between phthalimides of the formula,

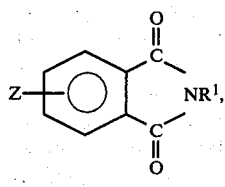

(3)

where Z is a radical selected from the class consisting of nitro, halo, fluoro, bromo, etc., and $R^1$ is as previously defined, and alkali diphenoxide of the formula,

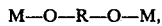

(4)

where R is as previously defined, and M is a metal ion of an alkalide metal selected from the class consisting of sodium, potassium, lithium, etc.

Included by the alkali diphenoxides of formula (4), are sodium and potassium salts of the following dihydric phenols,
2,2-bis(2-hydroxyphenyl)propane;
2,4'-dihydroxydiphenylmethane;
bis-(2-hydroxyphenyl)methane;
2,2-bis-(4-hydroxyphenyl)propane hereinafter identified as "Bisphenol-A" or "BPA";
1,1-bis-(4-hydroxyphenyl)ethane;
1,1-bis-(4-hydroxyphenol)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfoxide;
4,4'-dihydroxydiphenyl sulfide;
hydroquinone;
resorcinol;
3,4'-dihydroxydiphenylmethane;
3,4'-dihydroxybenzophenone;
4,4'-dihydroxybenzophenone; and
4,4'-dihydroxydiphenylether.

A more complete understanding of the practice of the method of the present invention can be obtained by reference to the drawing.

There is shown an aromatic bis(ether imide), or "bisimide" melt tank and a tank for an aqueous mixture of the phthalic acid and imide-anhydride exchange catalyst which is fed into a horizontal reactor, and the resulting imide-anhydride exchange reaction mixture is then fed into a holding tank followed by conveying the resulting mixture from the holding tank into an extraction column, which thereafter is fed into a vertical thin film evaporator resulting in the separation of aromatic bis(ether ahydride), or "bisanhydride" from the bottom of the thin film evaporator and recovery of an aqueous mixture of phthalic acid and imide-anhydride exchange catalyst, such as trimethylamine, triethylamine, tripropylamine, etc., from the top of the vertical thin film evaporator.

More particularly there is shown at 10 a bisimide melt tank with an agitator at 11 and a heated feed line at 12 which conveys the molten bisimide to the reactor 30. Simultaneously, an aqueous mixture of phthalic acid and imide-anhydride exchange catalyst is fed via 21 into tank 20 which is passed through a heat exchanger at 22 before it is conveyed through a heated line to reactor 30. Thorough mixing of the molten bisimide and the aqueous phthalic acid feed, which are maintained at flow rates sufficient to provide a ratio of 4 to 10 moles of phthalic acid per mole of bisimide, is achieved by passing the two feed streams through a mixing zone at 31 prior to entering reactor 30. The heat exchanger at 22 is operated to advance the temperature of the phthalic acid mixture to 200° C. After a residence time of about 10 minutes or less in the reactor at temperatures of 200° C. to 220° C., and pressure of 300 psi to 500 psi, the mixture is then fed through a heated line at 33 into a holding tank at 40. A valve at 32 provides a means for sampling the mixture from reactor 30. The imide-anhydride exchange mixture is then fed through a heated line at 41 into an extractor at 50 at a temperature of about 200° C. Extraction solvent is fed into the extractor after passing through a heat exchanger at 42 to bring the solvent up to a temperature of approximately 200° C. prior to being fed into the extractor 50. Suitable extraction solvents are, for example, toluene, benzene, chlorobenzene, o-dichlorobenzene, etc. An organic solvent solution of the imide-anhydride extraction, for example, N-organophthalimide, bisimide, etc., is passed through a heat exchanger at 52 and recovered for recycling. An aqueous exchange mixture is separated at the bottom of extractor 50 and fed into a vertical thin film evaporator at 60 through line 51. Rotating wiper blades at 61 facilitate the evaporation of an aqueous mixture of phthalic acid and imide-anhydride exchange catalyst which is condensed in heat exchanger 62. The desired bisanhydride in a molten state is recovered at 63.

Preferably the imide-anhydride exchange catalyst is a trialkylamine, for example, triethylamine, tributylamine, etc., while triethylamine is particularly preferred.

In order that those skilled in the art will be better able to practice the present invention, the following example is given by way of illustration and not by way of limitation. All parts are by weight.

EXAMPLE

In accordance with the drawing, molten 2,2-bis[4-(N-methylphthalimide-4-oxy) phenyl]propane was fed into the reactor which was filled with Koch static mixers of the Koch Engineering Company, New York, N.Y. The reactor, about 10 feet long and about 3 inches in diameter, maintained at a temperature of about 200° C. and 500 psi. Simultaneously, an aqueous solution of phthalic acid and triethylamine having 2 moles of triethylamine per mole of phthalic acid was pumped through a heat exchanger and brought up to a temperature of about 200° C. and fed through a separate line into the reactor. The aqueous phthalic acid mixture was pumped into the reactor at a flow rate sufficient to maintain a ratio of about 6 moles of phthalic acid, per mole of the aromatic bis(ether phthalimide).

The resulting imide-anhydride exchange mixture had a residence time of about 7-8 minutes in the reactor. The resulting equilibrated reaction mixture was collected in a holding tank maintained at a temperature of about 100° C.-200° C. and a pressure of about 70 to 300 psi. An analysis of a sample obtained from the exchange mixture showed that equilibrium had been obtained within 3-4 minutes.

The equilibrated reaction mixture was fed into a toluene extraction column maintained at 200° C. and 500 psi. After three extractions, there was obtained an aromatic bis(ether anhydride) product having at least 97 mole percent of 2,2-bis[4-(3,4-dicarboxyphenoxy)phenyl]propane dianhydride. Recovery of the aromatic bis(ether anhydride) was achieved by feeding the mixture into a thin film evaporator to effect the separation of molten aromatic bis(ether anhydride) at the bottom and aqueous phthalic acid and exchange catalyst at the top.

It was further found that the concentration of phthalic acid in the aqueous phthalic acid-triethylamine mixture, having 2 moles of triethylamine, per mole of phthalic acid, had a dramatic effect on the production rate of the aromatic bis(ether anhydride). For example, in 10 production runs of 12-20 hours each, the concentration of the phthalic acid was varied over a range of from about 20% to about 30% by weight in the phthalic acid-triethylamine feed mixture. A feed having a 20% phthalic acid concentration provided an aromatic bis(ether phthalic anhydride) production rate of 6 pounds per hour. However, in instances where the aqueous phthalic acid-triethylamine solution had a 28% by weight of phthalic anhydride and a viscosity of about 65 centistokes at 25° C., a production rate of about 30-35 pounds per hour was achieved.

The above results establish that the viscosity of the phthalic acid-triethylamine feed mixture, or correspondingly the weight percent of the phthalic acid utilized in the phthalic acid-triethylamine feed mixture is a significant factor in influencing the production rate of the aromatic bis(ether phthalic anhydride). Preferable, the phthalic acid-triethylamine feed mixture should have a viscosity of about 25 centistokes to 90 centistokes at 25° C. or a weight percent of phthalic anhydride of about 25% to 35%, based on the weight of the aqueous phthalic anhydride-triethylamine feed mixture to provide an optimum production rate for the aromatic bis(ether phthalic anhydride).

Although the above example is directed to only a few of the very many variables which can be used in the practice of the method of the present invention, it should be understood that the present invention is directed to a much broader method of making aromatic bis(ether phthalic anhydride)s based on the employment of a variety of aromatic bis(ether phthalimide)s, various triorgano amine catalysts and other concentrations of phthalic anhydrides in the aqueous phthalic anhydride-triorgano amine mixture.

What we claim as new and desire to secure by Letters Patent of the United States is:

1. In the process of making aromatic bis(ether phthalic anhydride) through an imide-anhydride exchange reaction, comprising heating a mixture of aromatic bis(ether phthalimide), phthalic anhydride, water and an triorganoamine exchange catalyst, whereby extended reaction periods, or venting of the reaction mixture is required, the improvement which comprises, forming the imide-anhydride reaction mixture by intermixing the aromatic bis(ether imide) while in the molten state with an aqueous mixture of phthalic acid containing 25-35% phthalic acid by weight and a triorgano amine and extracting the resulting aqueous mixture with an organic solvent.

2. A process in accordance with claim 1, where the phthalic acid-triorgano amine mixture has a viscosity of 25 centistokes to 90 centistokes.

3. A process in accordance with claim 1, where the triorgano amine exchange catalyst is triethylamine.

4. A process in accordance with claim 1, where the aromatic bis(ether imide) is 2,2-bis[4-(3,4-dicarboxyphenoxy)phenyl]propane-bis-N-methylimide.

5. A method in accordance with claim 1, where the aromatic bis(ether phthalic anhydride) is 2,2-bis[4-(3,4-dicarboxyphenoxy)phenyl]propane dianhydride.

* * * * *